United States Patent [19]

Brantigan

[11] Patent Number: 5,192,327
[45] Date of Patent: Mar. 9, 1993

[54] SURGICAL PROSTHETIC IMPLANT FOR VERTEBRAE

[76] Inventor: John W. Brantigan, 328 Overlook Brook Ct., Chagrin Falls, Ohio 44022

[21] Appl. No.: 673,474

[22] Filed: Mar. 22, 1991

[51] Int. Cl.$^5$ .................................................. A61F 2/44
[52] U.S. Cl. ...................................... 623/17; 606/60; 606/61
[58] Field of Search ....................... 623/17; 606/60, 61

[56] References Cited

U.S. PATENT DOCUMENTS

| | | |
|---|---|---|
| 2,677,369 | 5/1954 | Knowles . |
| 3,848,601 | 11/1974 | Ma et al. . |
| 3,867,728 | 2/1975 | Stubstad et al. .................... 623/17 |
| 4,309,777 | 1/1982 | Patil . |
| 4,349,921 | 9/1982 | Kuntz . |
| 4,553,273 | 11/1985 | Wu . |
| 4,714,469 | 12/1987 | Kenna . |
| 4,743,256 | 5/1988 | Brantigan . |
| 4,759,766 | 7/1988 | Buettner-Janz et al. .............. 623/17 |
| 4,834,757 | 5/1989 | Brantigan . |
| 4,878,915 | 11/1989 | Brantigan . |
| 4,997,432 | 3/1991 | Keller ............................... 623/17 X |

OTHER PUBLICATIONS

Cloward, R. B.: Vertebral Body Fusion for Ruptured Cervical Discs-Description of Instruments and Operative Technique; Am. J. Surg 98, Nov. 1959; 722–727.
Crock, H. V.: Practice of Spinal Surgery, Springer-Verlag, Wein, N.Y., 1983: pp. 35–92.
Flesh, H. R. et al.: Harrington Instrumentation and Spine Fusion for Unstable Fracture and Fracture-Dislocations of the Thoracic and Lumbar Spine The Journal of Bone and Joint Surgery, American Volume, vol. 59A, No. 2 Mar. 1977.
Flynn, J. C. et al.: Anterior Fusion of the Lumbar Spine; Journal of Bone and Joint Surgery; vol. 61A No. 8 Dec. 1979.
Kaneda, K. et al.: Burst Fractures with Neurologic Deficits of the Thoracolumbar-Lumbar Spine Results of Anterior Decompression and Stabilization with Anterior Instrumentation; Spine, vol. 9 No. 8, Nov.-Dec. 84 by J. B. Lippincot Company.
Robinson, R. A. et al.: The Results of Anterior Interbody Fusion of the Cervical Spine; The Journal of Bone and Joint Surgery, 4A No 8 Dec. 1962.
Simmons, E. H. et al.: Anterior Cervical Discectomy and Fusion; The Journal of Bone and Joint Surgery, 51B No. 2, May 1969.
Stauffer, R. N. et al.: Anterior Interbody Lumbar Spine Fusion; The Journal of Bone and Joint Surgery, 54A, No. 4, Jun. 1972.
White, A. B. et al.: Relief of Pain by Anterior Cervical-Spine Fusion for Spondylosis; The Journal of Bone and Joint Surgery, 55A No. 3 Apr. 1973.

Primary Examiner—Randall L. Green
Assistant Examiner—Dinh Nguyen

[57] ABSTRACT

Surgical prosthetic modular implants used singularly or stacked together are provided to support and fuse together adjacent vertebrae or to totally or partially replace one or more vertebrae in a vertebral column. The implants are rigid annular plugs, dimensionally similar to normal vertebral bodies, have simplified oval or hemi-oval shapes with ridged faces to engage adjacent vertebral bodies to resist displacement and allow bone ingrowth and fusion and to interdigitate with the ridges of an adjacent plug for modular stacking to allow variability of ultimate implant height. The implants can be provided in sets of different thicknesses and are internally grooved to receive an upstanding connecting bar to bind together the individual stacked implants into a stable unit. The annular implants have ample spaces to allow ingrowth of blood capillaries and packing of bone graft and are preferably made of a radiolucent material, preferably biocompatible carbon fiber reinforced polymers or are alternately made of traditional orthopaedic implant materials such as nickel, chromium, cobalt, stainless steel or titanium.

14 Claims, 3 Drawing Sheets

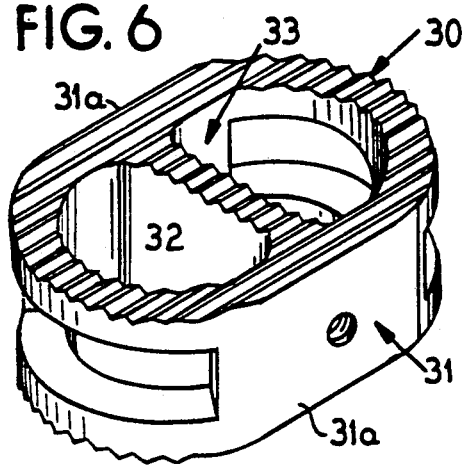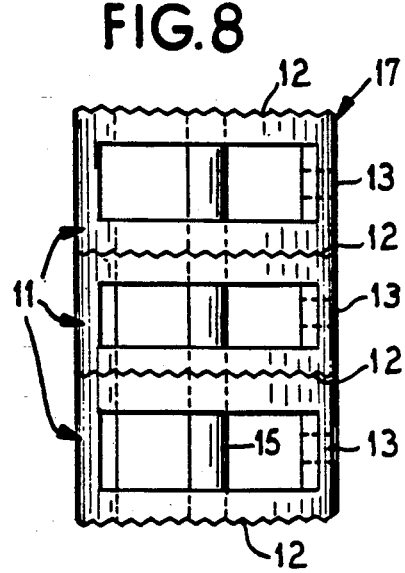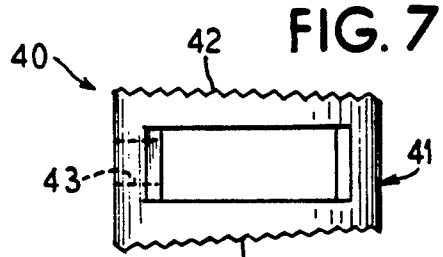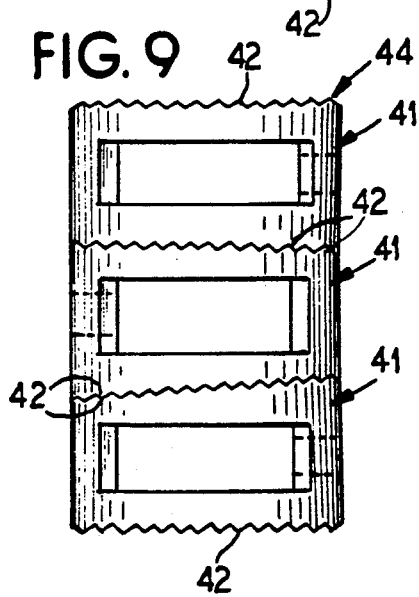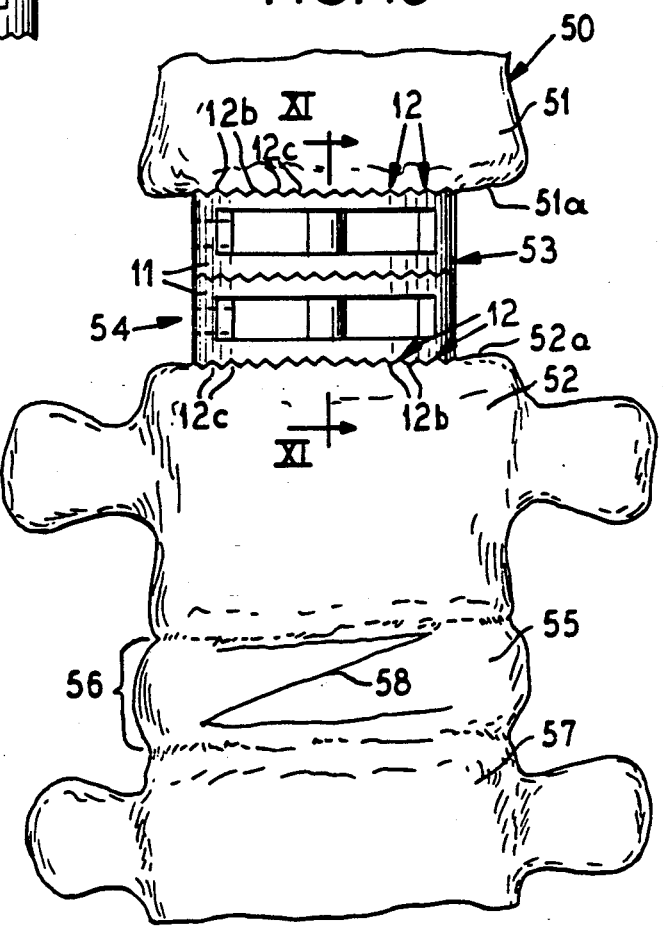

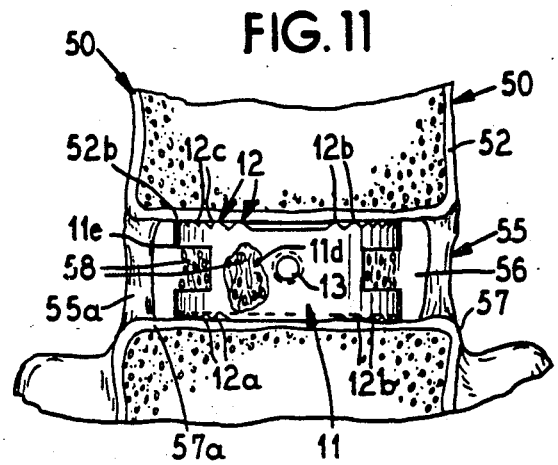
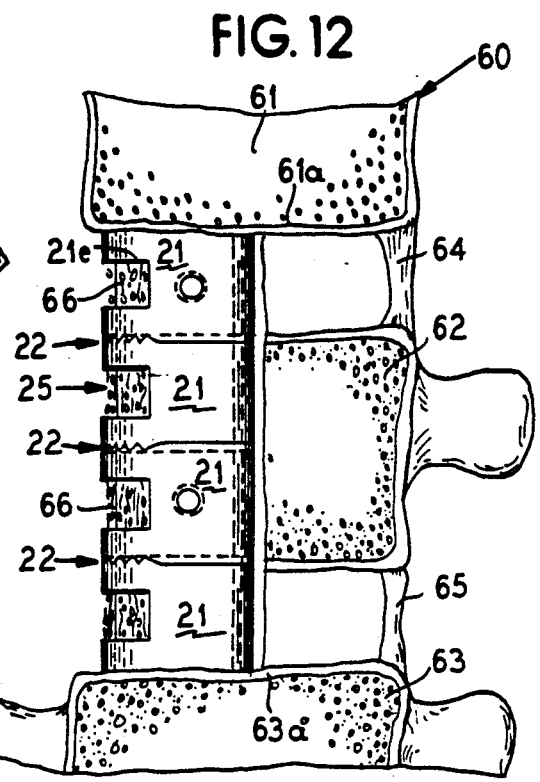
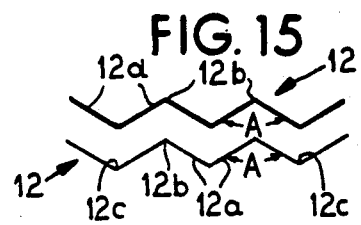
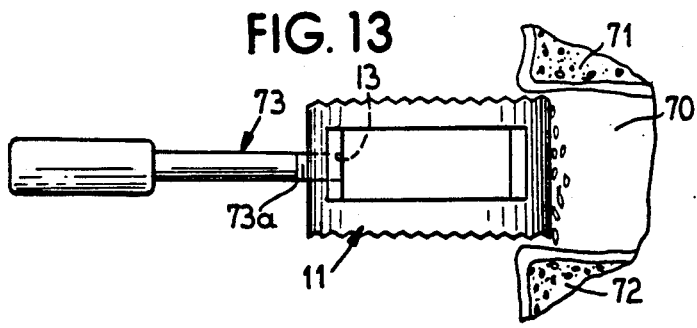
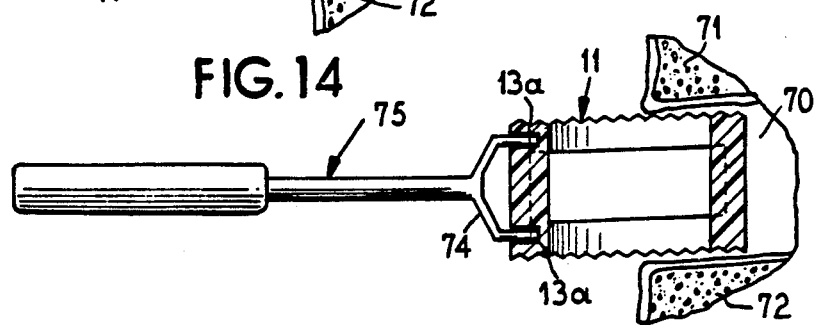

SURGICAL PROSTHETIC IMPLANT FOR VERTEBRAE

BACKGROUND OF THE INVENTION

1. Field of the Invention

This invention relates to inert rigid vertebral prosthetic devices and methods for implanting the devices between adjacent vertebrae to treat or prevent back or neck pain in patients with ruptured or degenerated intervertebral discs and for replacing vertebral bodies damaged by fracture, tumor or degenerative process. Specifically, the invention deals with ring-like prosthetic plugs or discs used singly or stacked together between vertebrae to form-support sturts in the spinal column and having rigid surfaces facilitating anchoring and providing valleys for bone ingrowth from adjoining vertebrae. The rings are bottomed on the opposing end faces of adjoining vertebrae, are preferably oval shaped with medial-lateral and anterior-posterior dimensions in the same ratio as normal vertebral bodies, are supplied in different heights to be used individually to replace a single damaged intervertebral disc, have ridges to bite into the vertebrae or to interdigitate to be securely stacked together to the exact height required at the time of surgery, have slots and hollow areas for packing bone graft material, tool receiving means, and are preferably radiolucent to allow visualization of the bone healing postoperatively.

2. Description of the Prior Art

While many types of vertebral prosthetic devices have been proposed, the success ratio has been very low and the surgical procedures have been very complicated and traumatic to the patient. The surgical implant devices and methods covered in my U.S. Pat. Nos. 4,743,256; 4,834,757 and 4,878,915 have greatly improved the success rate and have simplified the surgical techniques in interbody vertebral fusion. In the procedures covered by these patents, biologically acceptable but completely inert strut plugs are bottomed in channels or grooves of adjoining vertebrae and receive bone ingrowth which quickly fuses the structure to the bone and forms a living bone bridge across the fusion area.

The present invention now further improves this art of interbody fusion without cutting grooves or channels in the vertebrae and is especially well suited for anterior cervical and lumbar fusion. The invention provides ring-like prosthesis plugs or discs bottomed on end faces of adjoining vertebrae and constructed and arranged so that they can be used singly or stacked plurally to accommodate individual surgical requirements. The rings can replace excised discs and vertebrae and can also be mounted inside the fibrous disc column connecting adjoining vertebrae. The annular units are preferably oval or partial oval shaped preferably hemi-oval, to conform with vertebral disc shapes, have ridged or peaked surfaces for biting into the vertebrae on which they are seated and for receiving bone ingrowth in valleys between the peaks. When stacked, an interior connecting bar can be provided to lock the components in fixed relation and cooperate with interfitting ridges.

SUMMARY OF THE INVENTION

According to this invention, biologically acceptable, but inert rigid annular prosthesis units are provided to support and fuse with adjacent vertebrae in both the cervical, thoracic spine and lumbar portions of a human vertebral column. These ring-like prosthetic devices are bottomed on the hard bone faces or end plates of adjacent vertebrae and are generally oval shaped to conform with the general outline perimeter of the vertebrae. They are also provided in partial (preferably hemi-oval) annular shape to accommodate those surgical procedures where only a portion of the vertebrae or disc is damaged. Two such hemi-oval rings can be used in the posterior lumbar area in side-by-side relation since the dural sac and nerve roots must be retracted to each side in turn as the implant is placed on the opposite side. In an anterior fusion since the entire front of the disc space is exposed, a single piece implant can be used making the oval an advantage in this area.

The periphery of the oval ring is grooved to accommodate ingrowth of blood capillaries and the open central portion of the ring is preferably packed with bone graft material to facilitate bone ingrowth. Bone graft can also be packed in the grooves.

Each of the oval implants is sized to match the height of an average disc and thus, can vary from 10 to 15 mm for the lumbar area and from 7-11 mm for the cervical area.

The oval shape simplifies the surgical procedure since it can be rotated or reversed and still fit the vertebrae. Further, the device stretches the disc tissue creating a tension which will cause the vertebrae to tightly grip the ring on which it is bottomed. If the disc columnar tissue is preserved, a cut, preferably "Z"-shaped, can be made in the columnar fibrous tissue, the interior pulpus material of the disc removed, and the ring implant inserted through the cut to be bottomed on the adjoining vertebrae and surrounded by the disc tissue.

To accommodate a myriad of different heights between vertebrae on which the prosthesis ring is to be bottomed, the rings can be supplied in sets of different heights to be stacked to the exact height required for a particular surgical implant. For example, in the cervical spine, cervical corpectomy is often required for cervical myelopathies in which large bone spurs cause spinal cord pressure. An average grafting height is 30 mm after corpectomy and this can be achieved by stacking, for example, three 10 mm high oval implants.

In the treatment of thora columbar fractures, hemi-corpectomy is often done followed by grafting. Placement of stacked hemi-oval implants in the hemi-corpectomy area provides solid structural weight bearing. The re-sected vertebral bone is packed into the implant so that harvesting of additional bone grafting can be avoided.

In the treatment of vertebral tumors, the stacked oval implants can achieve solid bony fusion across the entire re-sected area providing a permanent mechanically secure repair with living tissue.

The invention now provides vertebral prosthetic implant devices suitable for anterior, posterior or lateral placement in any area of the spine requiring replacement of disc or vertebral body. Since the implants are intended to bottom out on adjacent vertebral end faces, which preferably have been prepared by flattening with a burr drill, removing cartilaginous material and stretching the annular fibrosis so that the vertebrae can tightly grip the plug, the plugs can be inserted either anteriorly, posteriorly or laterally into the vertebral column while mounted on the end of an insertion tool.

The ring devices have ridged surfaces providing multiple purposes of gripping the vertebrae to resist expulsion, forming valleys to facilitate bone ingrowth, and to matching interdigitate with each other for stacking.

An upstanding longitudinal connecting member fits in interior grooves in the ring and cooperates with the ridges to prevent separation of stacked implants in every direction except in longitudinal height. Since the implants are placed in compression between the vertebral bodies, they cannot come apart after implantation.

The implants are preferably made of radiolucent material such as carbon fiber reinforced polymers known commercially as "Peek", (polyetherether ketone) or "Ultrapek" (polyether ketone, ether ketone, ketone). Alternately, polycarbonate, polyprophylene, polyethelyene and polysulfone type plastics material filled with glass or carbon fibers can be used. Such materials are supplied by ICI Industries of Wilmington, Del.; Fiber-Rite Corporation of Winona, Minn. or BASF Corporation.

Preferred best mode embodiments of the invention are illustrated in the attached drawings in which:

FIG. 6 is a view similar to FIG. 1 but illustrating a modified device with an integral cross bar;

FIG. 7 is a side view showing a tapered device of this invention;

FIG. 8 is a side view of the stack of devices of FIG. 4 showing how the ridges interdigitate when stacked;

FIG. 9 is a view similar to FIG. 8 but showing a stack of tapered devices of FIG. 7 with the center device rotated 180° to form a vertical stack with end faces tapered in the same direction.

FIG. 10 is an elevational view of a portion of a vertebrae column showing a two stack assembly in an excised disc space between adjacent vertebrae and the manner in which a disc can be cut to receive a device of this invention.

FIG. 11 is a sectional view along the line XI—XI of FIG. 10;

FIG. 12 is a longitudinal view of a portion of a vertebral column, with parts in section and broken away to show the manner in which a stack of the devices is used to replace partially damaged discs and an intermediate vertebrae portion;

FIG. 13 is side diagrammatic view showing the insertion of a device of this invention in a disc space with the aid of a mounting tool.

FIG. 14 is a view similar to FIG. 13 illustrating the manner in which a fork-like tool can have tines mounted in a pair of holes in the device.

FIG. 15 is a line diagram illustrating the manner in which the ridges of the plugs have side walls diverging at the same angles from the peaks to provide interdigitating or complimentary mating or nesting projections.

As shown on the drawings:

Figure 1:
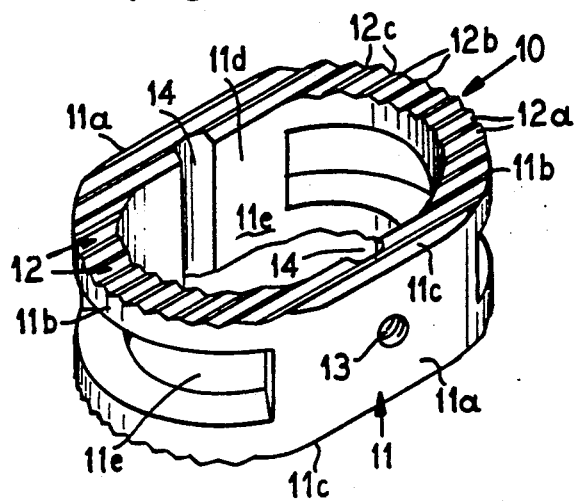
FIG. 1 is a top and side perspective view of a full oval prosthetic device according to this invention.

In FIG. 1, the reference numeral 10 designates generally a vertebrae prosthesis device of this invention composed of rigid biologically acceptable and inactive material, preferably a radiolucent plastics material, inert metal and the like as described above. The device 10 is an oval ring plug 11 generally shaped and sized to conform with the disc space between adjoining vertebrae in a vertebral column. The plug 11 has opposed sides 11a and ends 11b, flat, ridged top and bottom faces 11c and a central upstanding aperture 11d therethrough. The ends 11b have relatively wide and long horizontal peripheral slots 11e therethrough preferably extending into the sides 11a and communicating with the central aperture 11d.

Ridges 12 are formed longitudinally across the end faces 11c. These ridges 12 have inclined side walls 12a merging at sharp peaks 12b and provide valleys 12c between the side walls. The valleys 12c open at the ends 11b of the oval ring plug 11.

One side wall 11a of the plug 11 has an internally threaded hole 13 extending partially through the wall for receiving a mounting tool as hereinafter described.

Figure 3:
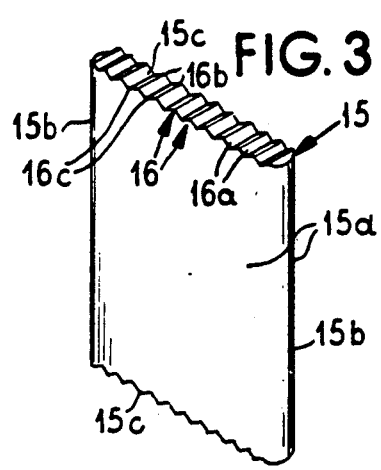
FIG. 3 is a top and side perspective view of a connecting bar fitting the illustrated grooves in the devices of FIGS. 1 and 2 to hold a plurality of the devices in stacked relation.

The interior faces of the side walls 11a also have upstanding open ended vertical grooves 14 preferably of fragmental cylindrical configuration. These grooves are provided for mounting a rectangular connecting bar 15 shown in FIG. 3. This bar 15 has flat side faces 15a, rounded side edges 15b to snugly fit the grooves 14 and top and bottom end edges 15c which are provided with ridges 16 that conform with the ridges 12 of the plug 10. Thus, these ridges 16 have oppositely inclined sides 16a converging to peaks 16b and providing valleys 16c therebetween. The peaks and valleys of the ridges on the ends of the connecting bar 15 are aligned with the peaks and valleys of the ridges on the top and bottom faces 11c of the plug 11 when the bar is seated in place in the grooves 14.

Figure 4:
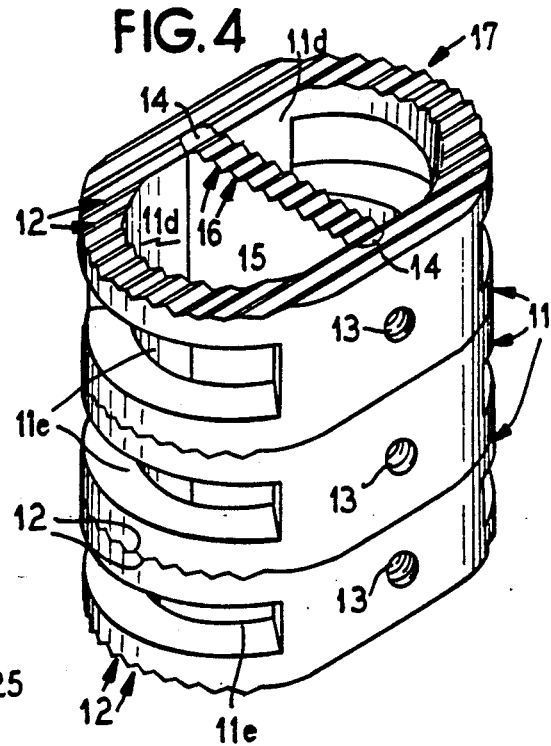
FIG. 4 is a top and side perspective view of a stack of the devices of FIG. 1 with the connecting bar of FIG. 3 in place.

The connecting bar 15 has a height conforming with the total height of a stack 17 of plugs 11 shown in FIG. 4 or with only a single plug 11 if a stack of plugs is not necessary. As shown in FIG. 4 three plugs 11 are stacked together with the ridges 12 of the intermediate plug nested in and interdigitating with the ridges of top and bottom plugs. These ridges interfit to provide a stable stack and the connecting bar 15 seated in the aligned grooves 14 of the three plugs will prevent shifting of the stack. The end faces of the bars 15 will then have their ridges 16 aligned with the ridges 12 in the exposed end faces of the top and bottom plugs 11.

The central aperture 11d of each plug 11 is separated by the bar 15 into two side-by-side chambers which are easily packed with bone graft material to expedite the fusion of the prosthesis device in the spinal column. In addition, the slots 11e in the ends 11b of the plugs can receive bone graft material and also provide free spaces for blood flow to speed up the fusion process.

Figure 2:
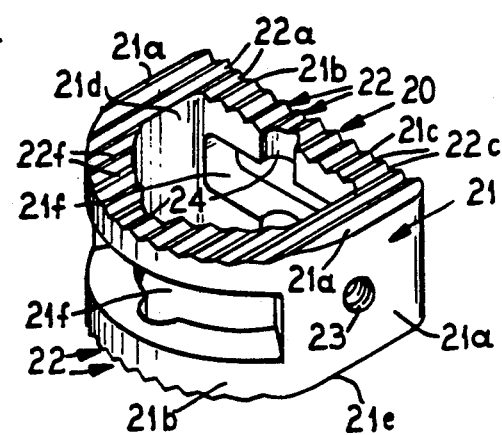
FIG. 2 is a top and side perspective view of a hemi-oval prosthetic device of this invention.

A modified hemi-oval device 20 is illustrated in FIG. 2 for usage in partial corpectomy operations and also for use in spaced side-by-side relation when an intermediate nerve space is needed. The device 20 is a one-piece plastics material or metal plug 21 of generally hemi-oval shape with opposed side walls 21a, a rounded oval end wall 21b, a flat opposite end wall 21c and a central aperture 21d. The top and bottom faces 21e of the plug 21 are ridged in the same manner as the plug 11 thus providing longitudinal ridges 22 with inclined side walls 22a, peaks 22b and valleys 22c. The end walls 21b and 21c have the same slots 21f as the slots 11e of the plug 11 and an end wall 21a has the same tool receiving recess 23 as the plug 11.

Internal grooves 24 are provided in the inner faces of the end walls 21b and 21c of the plug 21 to receive a connecting bar such as 15. This bar however will divide the central aperture of the plug 21 in a longitudinal instead of a transverse direction as illustrated for the plugs 11.

Figure 5:
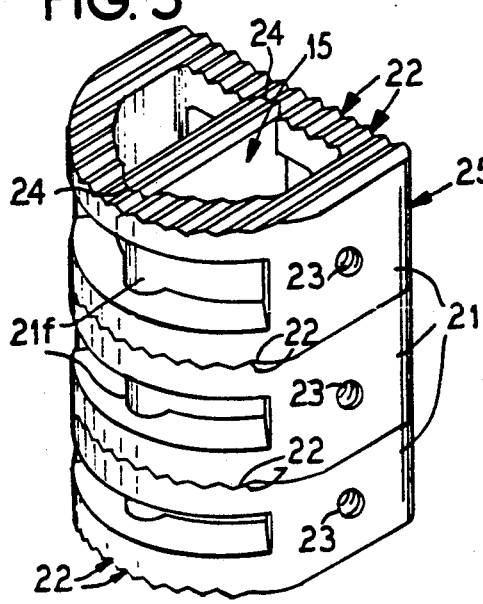
FIG. 5 is a top and side perspective view of a stack of the devices of FIG. 2 with a connecting bar like FIG. 3 in place.

As shown in FIG. 5 the plugs 21 form a stack 25, in the same manner as the plugs 11 in the stack 17 of FIG. 4 with the same type of connecting bar 15.

The plugs 11 and 21 of FIGS. 1 to 5 may vary in thickness or height to suit conditions and in the stacks of FIGS. 4 and 5, plugs of different thicknesses or heights can be stacked together to provide the desired overall height for each operation. Sets of these plugs may thus be supplied so that the surgeon can easily end up with a stack of the required height to fit the patient. The lengths or heights of the connecting bars 15 can also be varied to suit conditions or can be ground down at the time of the operation to match the stack.

The ridges on the exposed end faces of the stacks of plugs will bottom on the hard end faces or end plates of adjacent vertebrae and the apices or peaks 21b and 22g of these ridges will firmly engage and bite into these faces to prevent slippage. In addition, the valleys 12c and 22c between the ridges serve as gaps or troughs to freely receive bone ingrowth from the adjacent vertebrae.

The individual plugs or the stack of plugs can be introduced anteriorly, laterally or posteriorly depending upon conditions and the tool receiving recesses 13 and 23 of the plugs 11 and 21 can thus be positioned to meet the particular type of insertion into the vertebral column.

Instead of providing a separate bar or plate 15, as shown in FIG. 6, a modified device 30 of this invention is a plug 31 of the same oval shape as the plug 11 of FIGS. 1 and 4 but the reinforcing bar 32 of this plug is integral with its side walls 31a. The hollow interior 23 of the plug 31 is thus bisected by an integral internal partition 32 forming a pair of side-by-side apertures through the plug adapted to receive bone graft material.

A plug similar to 30 can also be provided in a hemi-oval shape. The plugs with the integral dividing bar are preferably used singly but also can be stacked and interdigitated by their ridges.

The plugs 11, 21 and 31 of FIGS. 1, 2 and 6 are uniform in thickness or height across their length.

In a further modified device 40 shown in FIG. 7, the plug 41 is tapered to be higher or thicker at its anterior end than at its posterior end. The plug 41 has ridged top and bottom faces 42, the same as the plugs of FIGS. 1-6 and a tool receiving recess 43 is provided in its higher or trailing end. By way of an example, the trailing end could be 12 mm in height while the leading end reduced to 9 mm in height.

In the stacking of plugs, each of which have uniform height or thickness such as shown at 11, 21, and 31, the holes for the mounting tool can all be aligned on one side of the stack as illustrated in FIG. 8 but, as shown in FIG. 9, the forming of a stack 44 of tapered plugs 41 requires displacement of the central or middle plug 180° from the end plugs in order that the stack will have a vertical column contour. The ridged faces 42 of the tapered plugs 41 will interdigitate and the exposed end faces of these ridges will be inclined or tapered to suit surgical application in spaces where the adjacent vertebrae are wider at one end than at the other. The use of the tapered plugs eliminates some of the grinding of the end faces of the vertebrae that may be needed for a good matching of the ridges with the vertebrae faces.

As shown in FIG. 10, a portion of a human vertebral column 50 has adjoining vertebrae 51 and 52 fused together by a two-unit stack 53 composed of the plugs 11 illustrated in detail in FIGS. 1, 4 and 8. This stack 53 fits the disc space 54 between the vertebrae 51 and 52 and the top ridges 12 of the stack are bottomed on and bite into the bottom face or hard end plate of the upper vertebrae 51 while the bottom ridges 12 of the stack are bottomed on and bite into the upper face or hand end plate 52a. The peaks 12b of the ridges 12 firmly anchor the stack to the vertebrae but do not penetrate through the hard faces 51a and 52a of the vertebrae. The valleys 12c are exposed to the vertebrae faces and receive bone ingrowth from the vertebrae during the post-operative fusion.

As shown all of the disc has been removed from the disc space 54 and the stack 53 maintains the disc space at its normal height.

As shown in FIGS. 10 and 11, a vertebral disc 55 fills the disc space 56 between the vertebrae 52 and a lower vertebrae 57 of the vertebral column 50. A Z-shaped cut 58 through the tubular fibrous portion of the disc 55 provides access to the interior pulpus portion of the disc permitting its removal to receive a single plug 11 forming a rigid strut inside of the column of disc fibers 55a which remain attached to the bottom face 52b of the upper vertebrae 52 and the top face 57a of the lower vertebrae 57. As illustrated, the peaks 12b of the ridges 12 on the top and bottom faces of the plug 11 bite into the faces 52b and 57a and the valleys 12c between the peaks are openly exposed to these faces of the vertebrae.

As better shown in FIG. 11, the hollow interior 11d and the slots 11e of the plug 11 are packed with bone graft material 58 which can be conveniently harvested from the iliac crests of the patient's pelvic bone.

FIG. 12 illustrates a cervical portion 60 of a human vertebral column having an upper vertebrae 61, a middle vertebrae 62 and a bottom vertebrae 63 with a stack 25 like FIG. 5 but composed of four plugs 21 implanted to support the column. As shown, the top and bottom vertebrae 63 remain intact while the middle vertebrae 62 has been partially excised. The four hemi-oval plug units 21 are interdigitated together through their ridges 22 and a bar 15 such as shown in FIG. 5 can hold the units in an upright column. Discs 64 and 65 have also been partially excised to receive the stack 25 but their remaining tissue is anchored to their adjacent vertebrae.

The bottom face 61a of the upper vertebrae 61 and the top face 63a of the bottom vertebrae 63 are partially penetrated by the peaks of the ridges of the top and bottom plugs 21 to function as described above. Also, the hollow interiors of the hemi-oval plugs 21 and their slots 21e are filled with bone graft material 66.

During surgery, the spinal column is stretched to regain any lost disc space caused by herniation of the discs. This stretches the remaining disc tissue and as illustrated in FIGS. 13 and 14, the plugs of this invention such as the plugs 11 or a stack of the plugs, are inserted into the opened up disc space such as 70 between adjacent vertebrae 71 and 72, either anteriorly, laterally or posteriorly while mounted on a tool 73 having a single end 73a threaded into the internally threaded hole 13 of the plug 11 as illustrated in FIG. 13.

Alternately, the plug 11, as illustrated in FIG. 14 may have a pair of side-by-side holes 13a receiving the tine end 74 of a modified tool 75.

Tools such as 73 and 75 may also be replaced with other gripping tools which do not require amounting apertures in the end faces of the plugs.

As better shown in the line diagram of FIG. 15 the ridged faces such as 12 of twos stacked plugs such as 11 of FIG. 1 have equally inclined side walls 12a diverging from sharp peaks 12b at a relatively wide angle A to prevent formation of thin narrow fingers or teeth that could break off and narrow valleys that could block bone ingrowth. An angle of at least 30°–45° is preferred to provide wide ridges and open valleys.

From the above descriptions, it will understood that this invention now advances the art of vertebral column surgery and provides prosthetic devices used singly or stacked to desired heights, which fit the disc spaces between adjacent vertebrae, bottom on and bite into the vertebrae faces without penetrating the hard surfaces thereof and have ample chambers for ingrowth of blood capillaries and bone graft material to expedite bone ingrowth during a post-operative period. The devices do not require anchoring screws or penetration through the hard faces of the vertebrae and can be mounted inside the vertebral disc or along the side of a partially excised disc, or in the disc space of a completely excised disc.

I claim as my invention:

1. A prosthetic device to integrate with and support vertebrae in a vertebral column which comprises a plurality of inert generally oval shaped rings conforming in shape and size with hard end plates of vertebrae on which it is to be seated, each of said rings having ridged top and bottom faces adapted to selectively interdigitate with surfaces of adjacent rings to form a stack and having peaks to bite into the end plates of adjoining vertebrae together with valleys between the peaks to receive bone ingrowth from the vertebrae for fusing the vertebrae together through the rings.

2. The device of claim 1, wherein the peaks have side walls diverging at an angle of not substantially less than about 30°.

3. The device of claim 1, wherein the top and bottom faces of the rings fully mate together when the rings are used in a stack.

4. A prosthetic device for vertebral fusion which comprises a stack of annular rigid inert plugs having interiors and interdigitated ridged faces holding the plugs against displacement in the stack and ridged exposed end faces for bottoming on adjoining vertebrae, and a connecting bar extending through the stack holding the plugs in aligned position in the stack.

5. The prosthetic device of claim 4, wherein each of the plugs have diametrically opposed internal upstanding grooves receiving the connecting bar.

6. The prosthetic device of claim 4, wherein the plugs have an internal connecting bar divides the interiors of the annular plugs into side by side compartments.

7. A surgical prosthetic device adapted for fusing together adjoining vertebrae in a vertebral column which comprises a rigid inert annular plug sized and shaped to fit opposed end faces of vertebrae in a vertebral column and having top and bottom faces with peaks adapted to bite into the end faces of the adjoining vertebrae and valleys between the peaks to receive bone ingrowth, said plug selected from the group consisting of oval and hemi-oval rings, and said plug having a height effective to provide a strut between the vertebrae maintaining a desired disc space.

8. A surgical prosthetic device adapted for fusing together adjoining vertebrae in a vertebral column which comprises a rigid inert annular plug sized and shaped to fit opposed end faces of vertebrae in a vertebral column and having top and bottom faces with peaks adapted to bite into the end faces of the adjoining vertebrae and valleys between the peaks to receive bone ingrowth; said plug having a height effective to provide a strut between the vertebrae maintaining a desired disc space, and said height of the annular plug being sufficient to stretch a annulus fibrosis tissue of a disc connecting the adjoining vertebrae to maintain a desired disc height and provide snug gripping of the plug with the and faces of the adjoining vertebrae.

9. The surgical prosthetic device of claim 8 wherein the top and bottom faces of the plug have diverging equally sloping side walls converging to sharp peaks ,and relatively wide valleys between the peaks and said side walls adapted to nest together to hold adjacent plugs in alignment.

10. A surgical prosthetic device adapted for fusing together adjoining vertebrae in a vertebral column which comprises a rigid inert annular plug having an interior and sized and shaped to fit opposed end faces of vertebrae in a vertebral column and having top and bottom faces with peaks adapted to bite into the end faces of the adjoining vertebrae and valleys between the peaks to receive bone growth, said plug having a height effective to provide a strut between the vertebrae maintaining a desired disc space, and said plug having a bar intersecting the interior of the plug.

11. The surgical prosthetic device of claim 10 having diametrically opposed upstanding internal grooves adapted to receive said bar.

12. A prosthetic device seating on hard end plates of vertebrae in a vertebral column while preserving healthy disc tissue between the vertebrae which comprises a rigid inert annular plug generally conforming in shape and size with opposing hard end plates of vertebrae on which it is to be seated, said plug having peripheral side and end walls, top and bottom faces, a central aperture therethrough between the faces, and a peripheral slot therein, said end faces having raised ridges with side walls converging to peaks and valleys between the side walls, said peaks adapted to be bottomed on and bite into the hard end plate faces of vertebrae, tool mounting means in a peripheral wall of the plug, said aperture and slot in the plug adapted to be packed with bone graft material, and said plug being composed of a radiolucent plastics material.

13. A prosthetic device seating on hard end plates of vertebrae in a vertebral column while preserving healthy disc tissue between the vertebrae which comprises a rigid inert annular plug generally conforming in shape and size with opposing hard end plates of vertebrae on which it is to be seated, said plug having peripheral side and end walls, top and bottom faces, a central aperture therethrough between the faces, and a peripheral slot in each end wall therein, said end faces having raised ridges with side walls converging to peaks and valleys between the side walls, said peaks adapted to be bottomed on and bite into the hard end plate faces of vertebrae, tool mounting means in a peripheral wall of the plug, and said aperture and slot in the plug adapted to be packed with bone graft material.

14. A prosthetic device seating on hard end plates of vertebrae in a vertebral column while preserving healthy disc tissue between the vertebrae which comprises a rigid inert annular plug generally conforming in shape and size with opposing hard end plates of vertebrae on which it is to be seated, said plug having peripheral side and end walls, top and bottom faces, a central aperture therethrough between the faces, and a peripheral slot therein, said end faces having raised ridges with side walls converging to peaks and valleys between the side walls, said peaks adapted to be bottomed on and bite into the hard end plate faces of vertebrae, tool mounting means in a peripheral wall of the plug, said aperture and slot in the plug adapted to be packed with bone graft material and said plug having an anterior portion higher than the posterior portion to provide a wedging effect when inserted into position between the hard end plate faces of the vertebrae.

* * * * *

UNITED STATES PATENT AND TRADEMARK OFFICE
CERTIFICATE OF CORRECTION

PATENT NO. : 5,192,327
DATED : March 9, 1993
INVENTOR(S) : John W. Brantigan

It is certified that error appears in the above-indentified patent and that said Letters Patent is hereby corrected as shown below:

Column 8:
Claim 8, line 11 "a annulus" should read --annulus--.

line 14, "and faces" should read --end faces--.

Signed and Sealed this

Thirtieth Day of August, 1994

Attest:

BRUCE LEHMAN

*Attesting Officer*   *Commissioner of Patents and Trademarks*